(12) United States Patent
Becker et al.

(10) Patent No.: US 7,422,601 B2
(45) Date of Patent: Sep. 9, 2008

(54) METHOD FOR INDUCING HYPOTHERMIA

(75) Inventors: Lance B. Becker, Chicago, IL (US); Terry Vanden Hoek, Chicago, IL (US); Kenneth E. Kasza, Palos Park, IL (US)

(73) Assignee: University of Chicago Office of Technology Transfer, Chicago, IL (US)

( * ) Notice: Subject to any disclaimer, the term of this patent is extended or adjusted under 35 U.S.C. 154(b) by 379 days.

(21) Appl. No.: 11/124,958

(22) Filed: May 9, 2005

(65) Prior Publication Data

US 2005/0203598 A1     Sep. 15, 2005

Related U.S. Application Data

(63) Continuation of application No. 10/162,442, filed on Jun. 3, 2003, now Pat. No. 6,962,601, and a continuation-in-part of application No. 09/632,195, filed on Aug. 2, 2000, now Pat. No. 6,547,811, which is a continuation-in-part of application No. 09/586,576, filed on Jun. 2, 2000, now Pat. No. 6,413,444.

(60) Provisional application No. 60/146,753, filed on Aug. 2, 1999.

(51) Int. Cl.
*A61F 7/00* (2006.01)
(52) U.S. Cl. ....................... 607/105; 607/113
(58) Field of Classification Search ............... 607/96, 607/104–106, 113; 604/113
See application file for complete search history.

(56) References Cited

U.S. PATENT DOCUMENTS

| | | | |
|---|---|---|---|
| 3,425,419 A | 2/1969 | Dato | |
| 3,504,674 A | 4/1970 | Swenson et al. | |
| 3,987,211 A | 10/1976 | Dunn et al. | |
| 4,111,209 A | 9/1978 | Wolvek et al. | |
| 4,416,281 A | 11/1983 | Cooper et al. | |
| 4,474,016 A | 10/1984 | Winchell | |
| 4,605,006 A | 8/1986 | Jacques | |
| 4,745,922 A | 5/1988 | Taylor | |
| 4,872,866 A | 10/1989 | Davis | |
| 5,088,487 A | 2/1992 | Turner | |
| 5,262,055 A | 11/1993 | Bae et al. | |
| 5,415,222 A | 5/1995 | Colvin et al. | |
| 5,514,094 A | 5/1996 | Anello et al. | |
| 5,709,654 A | 1/1998 | Klatz et al. | |
| 5,722,482 A | 3/1998 | Buckley | |

(Continued)

OTHER PUBLICATIONS

Kasza, et al. *Assessment of Impact of Advanced Energy Transmission Fluids on District Heating and Cooling Systems(Phase I)*, Argonne National Laboratory,1987.

(Continued)

*Primary Examiner*—Roy D Gibson
(74) *Attorney, Agent, or Firm*—Brinks Hofer Gilson & Lione

(57) ABSTRACT

Systems for phase-change particulate slurry cooling equipment and methods to induce hypothermia in a patient through internal and external cooling are provided. Subcutaneous, intravascular, intraperitoneal, gastrointestinal, and lung methods of cooling are carried out using saline ice slurries or other phase-change slurries compatible with human tissue. Perfluorocarbon slurries or other slurry types compatible with human tissue are used for pulmonary cooling. And traditional external cooling methods are improved by utilizing phase-change slurry materials in cooling caps and torso blankets.

50 Claims, 10 Drawing Sheets

U.S. PATENT DOCUMENTS

| | | | |
|---|---|---|---|
| 5,755,756 | A | 5/1998 | Freedman, Jr. et al. |
| 5,807,318 | A | 9/1998 | St. Goar et al. |
| 5,837,003 | A | 11/1998 | Ginsburg |
| 5,902,299 | A | 5/1999 | Jayaraman |
| 5,916,242 | A | 6/1999 | Schwartz |
| 6,033,383 | A * | 3/2000 | Ginsburg .................... 604/113 |
| 7,077,825 | B1 * | 7/2006 | Stull .......................... 604/113 |

OTHER PUBLICATIONS

Kasza, et al. *Improvement of the Performance of Solar Energy and Waste Heat Utilization Systems by Using Phase-Change Slurry as an Enhanced Heat-Transfer Storage Fluid*, ASME J. Solar Eng. 107: 229-236, 1985.

Kasza, et al. *Ice Slurry Cooling Research: Storage Tank Ice Agglomeration and Extraction*, ASHRAE Transactions Annual Meeting, Seattle, WA, Jun. 1999.

Liu, et al. *Pressure Drop and Heat Transfer Characteristics of Particulate Slurry Channel Flows*, ASME FED vol. 75, 1988.

Hayashi, et al. *A Method for Measuring Ice Slurry Particle Agglomeration in Storage Tanks*, ASHRAE Presentation Winter Meeting, 1999.

S.V. Patanker, *Numerical Heat Transfer and Fluid Flow*, Hemisphere Series on Computational Methods in Mechanics and Thermal Science, Hemisphere Publishing, pp. 52-54, 1980.

Carslaw, et al. *Conduction of Heat in Solids*, Oxford University Press, 1973, pp. 233-237.

Idris, et al. *Does Hypoxia or Hypercarbia Independently Affect Resuscitation From Cardiac Arrest?*, Chest, 108(2): 522-25, 1995.

Idris, et al. *Effect of Ventilation on Resuscitation in an Animal Model of Cardiac Arrest*, Circulation, 90(6):3063-69 (1994).

Swindle, M.M. *The Use of Animals in Surgical Research*, J Invest Surg., 1(1): 3-4, 1988.

* cited by examiner

METHOD FOR INDUCING HYPOTHERMIA

RELATED APPLICATIONS

This application is a continuation of U.S. patent application Ser. No. 10/162,442, filed Jun. 3, 2003 now U.S. Pat. No. 6,962,601, by Lance B. Becker et al., entitled "Method for Inducing Hypothermia," which is a continuation-in-part of U.S. patent application Ser. No. 09/586,576, filed Jun. 2, 2000, by Kenneth E. Kasza, entitled "Method And Apparatus For Producing Phase Change Ice Particulate Saline Slurries," now U.S. Pat. No. 6,413,444 issued Jul. 2, 2002, and U.S. patent application Ser. No. 09/632,195, filed Aug. 2, 2000, by Lance B. Becker, Terry Vanden Hoek, and Kenneth E. Kasza, entitled "Method For Inducing Hypothermia," now U.S. Pat. No. 6,547,811 issued Apr. 15, 2003, each of which claims the benefit of priority under 35 U.S.C. §119(3) to U.S. Provisional Application No. 60/146,753, filed Aug. 2, 1999, by Kenneth Kasza et al., entitled "Method for Inducing Hypothermia."

FEDERALLY SPONSORED RESEARCH OR DEVELOPMENT

The United States Government has rights in this invention pursuant to Contract No. W-31-109-ENG-38 between the United States Department of Energy and the University of Chicago.

BACKGROUND OF THE INVENTION

The present invention relates to the production and use of engineered phase-change particulate slurries, such as ice slurries, with high cooling capacity, fluidity, and stability to induce protective hypothermia through internal and external cooling.

It is well known that hypothermia can postpone damage to tissues caused by inadequate blood flow and oxygen deprivation. One important example of the potential protective properties of hypothermia is in the area of cardiac arrest. Sudden cardiac arrest is one of the leading causes of death in the United States, affecting about 1,000 people every day, most of them outside of a hospital setting. Despite widespread use of basic life support and advanced cardiac life support by paramedics, survival of cardiac arrest patients is usually less than 2-4%, in large part because cells of the brain and the heart begin to die within minutes following global ischemia, or inadequate blood flow.

The ability of these cells to survive severe ischemia can be significantly enhanced by transient hypothermia. However, rapid and significant cooling (within 10 minutes, and to a temperature of 34° C. or less) of a patient without blood flow in a pre-hospital setting has been unachievable.

External cooling methods have not been found effective in achieving the desired rates of cooling. Several studies by the applicants highlight the fact that current techniques of surface cooling alone are not effective for the rapid induction of hypothermia. In patients with normal circulation, the core cooling rates achievable with external cooling blankets and/or evaporative convection methods do not exceed 0.1° C./min. with rates on the order of 0.05° C./min. being more typical. This results in a cooling rate of less than 6° C. per hour, not rapid enough for protective use during cardiac arrest. Even with complete immersion of a human in an ice slush water bath (0° C.), achieving a nearly maximally effective surface heat transfer coefficient, the lack of blood flow during cardiac arrest prevents achieving the desired protective core cooling rates.

Accordingly, there is a need for a rapid and safe method of internally cooling the target zones—the heart, the brain, and other regions, which can be used in an out-of-hospital setting. The rapid induction of protective hypothermia using internal phase-change slurry cooling can have a significant impact on the rate of survival for patients suffering from a variety of conditions including, but not limited to, ischemia due to cardiac arrest, myocardial infarction, and stroke, hemorrhage, traumatic injury, and asphyxia.

There are significant theoretical advantages to inducing hypothermia in ischemic patients under field conditions, including the ability to cool ischemia-sensitive organs like the heart and brain more rapidly, and, therefore, reduce tissue injury caused by the sudden reperfusion of normothermic ischemic tissue.

The physics of thermal heat-transfer creates a formidable challenge to rapid cooling of a human with little or no circulation. This is particularly problematic since the brain and heart are the targets of the cooling process. External methods of cooling can lower the temperature of these oxygen-sensitive organs but only very slowly at rates of less than 0.05° C./min (only 3° C./hr). The difficulty is that without a pulse or adequate perfusion, there is very little transfer of heat from the deeper tissues to the superficial tissues. External cooling techniques (i.e. cooling blankets or even full ice-water immersion) during conditions of no or low blood flow only cools core organs via direct tissue thermal conduction. Unfortunately, the speed of cooling with these techniques is too slow to avoid a lethal outcome due to ischemic reperfusion injury to vital organs, including the heart and brain.

BRIEF SUMMARY OF THE INVENTION

The present invention provides for the application of phase-change particulate slurry cooling systems, equipment, and methods designed for cooling patients rapidly and safely. Subcutaneous, intravascular, intraperitoneal, gastrointestinal, and lung methods of cooling are carried out using saline ice slurries or other phase-change slurries compatible with human tissue. Perfluorocarbon slurries or other slurry types compatible with human tissue are used for pulmonary cooling. And traditional external cooling methods are improved by utilizing phase-change slurry materials in cooling caps and torso blankets.

Since cardiac arrest represents a no or low blood flow state (low blood flow is achieved, for example, with chest compressions) in which cells begin to die within minutes, the rapid induction of moderate to profound hypothermia during cardiac arrest can serve a highly protective function. The use of high fluidity phase-change slurry materials with the capacity for effective internal cooling of such patients makes it possible to cool a victim of cardiac arrest within minutes. Rapid induction of hypothermia during cardiac arrest in a pre-hospital setting can significantly improve a patient's outcome by protecting cells of the brain and heart until blood flow can be reestablished at the hospital using existing cardiac bypass technology.

DETAILED DESCRIPTION OF THE INVENTION

Figure 1:
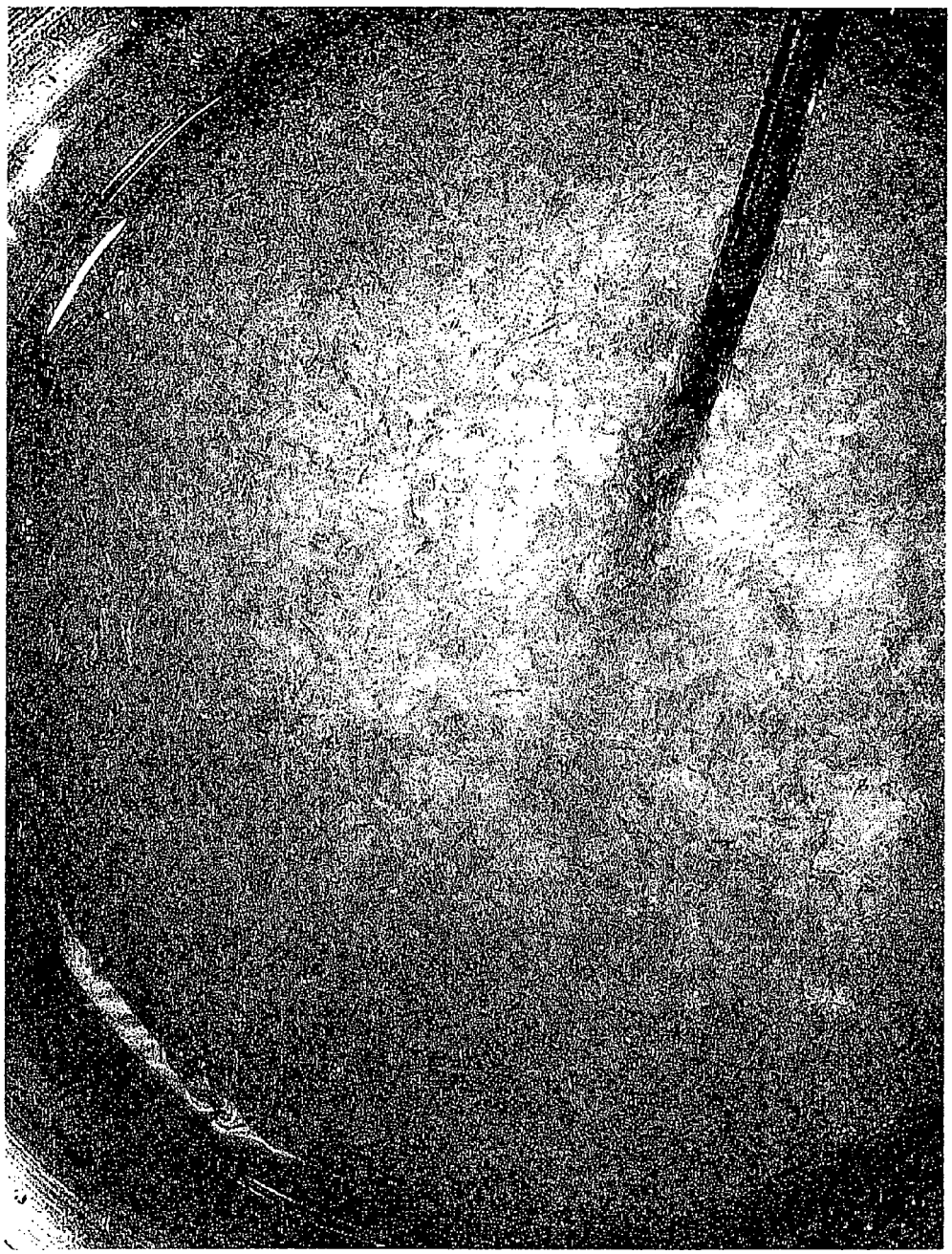
FIG. 1. Small 0.1 to 0.3 mm ice crystals formed in a beaker of 0.9% sodium chloride solution.

The present invention relates to the use of phase-change particulate slurries designed specifically for medical use and the cooling equipment used to rapidly induce hypothermia in a patient.

A phase-change particulate slurry comprises small particles of a phase-change media suspended in a transporting fluid. Preferably, the phase-change particulate slurry has a high heat of fusion. One example of such a phase-change material is ice, but other materials with a heat of fusion may also be used. Examples of transporting fluids include, but are not limited to, water, saline solution, and perfluorocarbon solution. The terms "slurry" and "phase-change slurry" are also used to refer to "phase-change particulate slurries," examples of which include, but are not limited to, saline ice slurries and perfluorocarbon slurries as discussed.

Hypothermia is defined as a body temperature significantly below 37° C. Various levels of hypothermia have been defined. Mild hypothermia is defined as a body temperature of about 34° C., moderate hypothermia as a body temperature of about 23-32° C., and profound hypothermia as a body temperature of about 12-20° C. (See Stedman's Medical Dictionary, 26th Edition, 1995.) The term "significant cooling" as used herein means cooling to a temperature of about 34° C. or less.

A preferred method for producing phase change particulate saline slurries, water and a first set amount of sodium chloride are provided to produce a saline solution. The saline solution is cooled to a specific temperature. A selected percentage of chunk ice is added to the saline solution and the chunk ice is broken into ice particles. The ice particles have a small size. Next a second set amount of sodium chloride is added and distributed for smoothing of the ice particles.

However, this is not to say that the preferred method is the only method of producing a phase change particulate saline slurry. For example, another method for producing phase change particulate saline slurries includes providing a liquid with a set percentage of freezing point depressant to form a first solution, such as, a set percentage saline solution; cooling the first solution to a set temperature to produce ice particles; and increasing an ice particle concentration under controlled temperature for a period of time to provide a set ice particle concentration for the phase change particulate saline slurry. Other methods are provided in the applications incorporated by reference.

In one embodiment, the slurry is delivered through a subcutaneous injection. The location of injection depends on the desired target for cooling. In one example of a subcutaneous injection, cooling of the brain and the heart are achieved through a pericarotid artery injection of a saline slurry or other suitable phase-change slurry into the soft tissues of the neck. The pericarotid soft tissues allow the 3-4 inches of exposed carotid artery and jugular vein in both sides of the neck to function as a heat exchanger for blood traveling to the brain and heart during CPR. This method of cooling may be used alone for selectively cooling the brain cooling, as desired, for example, with a stroke patient. Alternatively, this method can be used in combination with other cooling methods discussed below.

In another embodiment, the slurry is delivered through an intravascular injection. The vessel for injection is chosen based, in part, on the desired cooling target. In one example of delivery through intravascular injection, the heart is cooled through a direct aortic "flush" infusion using a saline phase-change slurry or other suitable phase-change slurry. In another example of delivery, an IV may be loaded with the slurry and the slurry introduced to the target through an introducer in the femoral artery. Cooling through injection of the slurry into other blood vessels is also possible.

In another embodiment, cooling is achieved by delivering the slurry intraperitoneally. For example, delivery can be through a percutaneous puncture of the intraperitoneal cavity.

In another embodiment, cooling is achieved by delivering the slurry through the gastrointestinal (GI) tract. Examples include rectal delivery or delivery through a nasogastric (NG) tube.

In yet another embodiment, an oxygenated sodium chloride saline or perfluorocarbon saline ice slurry or other suitable slurry is delivered to the lungs to achieve pulmonary cooling and cooling of the heart. Delivery of slurry to the lungs offers the advantage of a huge surface area for heat exchange and almost direct contact with the heart on one side while simultaneously providing oxygen. Cooling the lungs also cools the heart indirectly by inducing cooler blood flow from the lungs to the heart through CPR.

The methods of treatment described in each of the embodiments can be used alone or in any combination, depending on the condition of the patient, the target tissue for cooling, and the degree of cooling desired.

The present invention provides a treatment protocol for the induction of resuscitative hypothermia during cardiac arrest, stroke, or other conditions in which blood flow is restricted. In one example according to the present invention, in an emergency setting, paramedics at the scene of a cardiac arrest attempt the usual advanced cardiac life support therapies. If, however, these traditional methods fail, they initiate an additional series of procedures. First, with intubation and CPR already started, they inject the soft tissues in the pericarotid region bilaterally with a saline ice slurry to begin cooling of the brain. Next, they administer an oxygenated sodium chloride or perfluorocarbon ice slurry to the lungs to provide additional cooling to the heart and then brain while ventilating the patient. An aortic flush saline ice slurry adds additional cooling as they begin transporting the patient. Finally, external cooling of head and other surfaces begins while the patient is taken to the hospital.

With these combined methods, the patient is cooled to a protective temperature upon arrival at the emergency department 5-10 minutes later. Once at the hospital, a resuscitation team administers additional drugs to maintain critical cellular functions while cardiac bypass is established for the patient.

External Cooling

One aspect of the present invention provides improved surface cooling blankets. For cardiac arrest patients, conventional cooling blankets and head caps have not by themselves been able to supply anywhere near the protective cooling needed for the heart and brain. However, the use of external surface cooling, when used in conjunction with internal cooling phase-change ice slurries is still beneficial. Conventional blanket devices do not achieve the thermal boundary condition and cooling associated with immersion in an ice bath. Colder coolant medium temperatures would improve the cool-down rate, however, the risk of freezing tissue is increased.

Cooling blankets according to the present invention are improved through the implementation of phase-change materials that have transition temperatures near 0° C. and have improved blanket contact with the skin to reduce thermal contact resistance. There are conventional cooling blankets currently available which use phase-change media, however, these devices, when in their chilled state, are stiff and do not fit very snuggly or adapt to the shape of the head, neck, or torso. This causes a lack of contact with tissue (air gaps), and hence zones of greatly reduced heat transfer. Furthermore, these blankets are also often covered with a cloth outer layer which reduces skin contact and reduces cooling effectiveness.

According to the present invention, preferably, phase-change materials which exhibit less rigidity in the cooled state and have transition temperatures near 0° C. are used for blankets and other external cooling devices. Preferably, the coverings for containing the phase-change substances are very smooth, thin, compliant, and can be fabricated into slip-on devices for cooling the regions of interest. One example of such a covering material is plastic Mylar having a metallic coating. This material is very strong, produced in very thin layers, readily fabricated into complex form fitting shapes, and it is very smooth, reducing surface contact resistance. The contact resistance is further reduced by coating or wetting the areas to be cooled before applying the cooling device.

Internal Cooling

The present invention relates to methods of rapidly inducing hypothermia in a patient using phase-change particulate slurries for internal cooling. Cells within the brain and heart are the most sensitive among the tissues of the body to reduced blood flow and oxygen deprivation and are, therefore, the principle sites to protect first with hypothermia. The protection of resuscitative hypothermia is important in cardiac arrest, as well as other ischemic conditions including stroke, myocardial infarction, hemorrhage, traumatic injury, and asphyxia.

Brain Cooling

For cooling the brain, in addition to cooling the head externally, as discussed above, with cooling jackets or pads containing a phase-change material at a temperature of around 0° C., the carotid artery on each side of the neck is used over its length as a heat exchanger for cooling the blood transported directly into the brain. Likewise, the jugular vein, next to the carotid artery, which carries blood back to the heart can also be cooled. Much of the following discussion for carotid artery cooling also applies to cooling the jugular vein blood flow and the heart. In a cardiac arrest patient, blood flow is induced by chest compressions. The cooling of the carotid blood flow is greatly enhanced by injection of a saline ice slurry into both sides of the neck for near intimate contact between the artery external walls and the slurry. The slurry is not injected directly into the carotid artery or the jugular vein, but into the soft tissue surrounding these blood vessels.

One method of delivering the slurry for brain cooling through a neck injection is as follows: The operator first identifies the region of the carotid artery and the jugular vein in the neck. The skin is punctured with a needle and a catheter is inserted into the pericarotid region of the soft tissue of the neck. The external portion of the catheter is attached to a syringe containing the slurry. A specified volume of slurry is then injected into the soft tissues of the neck in the vicinity of the carotid artery and the jugular vein. Another method of delivery is to use a directed mechanical metered feed of slurry.

Heart Cooling

In addition to cooling the heart with externally applied cooling jackets or pads containing a phase-change material at a temperature of around 0° C., the present invention involves various methods of internal cooling which directly target the heart. In one embodiment, the heart is cooled in the same manner discussed above for cooling the brain. Injecting ice slurry into both sides of the neck for cooling blood flow to the brain from the carotid artery also cools blood flowing in the jugular vein returning directly to the heart.

In a second embodiment, the heart is cooled by charging the lungs with an oxygenated sodium chloride or perfluorocarbon slurry. Cooling the lungs results in heart cooling by taking advantage of the thermal conduction resulting from the close proximity of the lungs with one side of the heart.

In another embodiment, the lungs are charged with an oxygenated sodium chloride or perfluorocarbon slurry, and chest compressions move cool blood from the lungs into the heart, enhancing the rate of heart cooling.

In one method of delivering the slurry into the lungs, an endotracheal tube is inserted into the trachea. The external portion of the endotracheal tube is connected to a ventilation-type bag which has been specifically modified to deliver slurry. A specified volume of slurry is delivered to the lungs through the endotracheal tube.

The ventilation bag and delivery tube are modified to minimize slurry plugging the flow passages and to facilitate the controlled delivery of the required amount of slurry. The bag is also modified for interface with the chiller and other equipment needed to form the slurry. One alternate method of delivering slurry to the lungs is directly through a mechanical tube feed into the lungs.

In a third embodiment for heart cooling, the slurry is introduced through a direct aortic "flush" or infusion, producing cooling in the target zones. For the aortic flush, the slurry is delivered to the aorta through the use of a percutaneous open femoral artery puncture. A larger bore long catheter is advanced through the puncture toward the head until the catheter is in the region of the aortic arch. A syringe is attached at the external end of the catheter. The syringe is then loaded with slurry and a specified volume of slurry is pushed through the syringe and through the tubing into the aorta.

Phase-Change Slurries

Phase-change slurries in the form of high concentrations of small ice particles in a liquid carrier dramatically increase coolant capacity compared to other liquids such as water or blood that lack heat of fusion effects. Methods and apparatus for the production of phase-change slurries are discussed in greater detail in U.S. patent application Ser. No. 09/585,770, filed Jun. 2, 2000, by Kenneth E. Kasza, entitled "Method And Apparatus For Producing Phase Change Ice Particulate Perfluorocarbon Slurries," U.S. patent application Ser. No. 09/586,576, filed Jun. 2, 2000, by Kenneth E. Kasza, entitled "Method And Apparatus For Producing Phase Change Ice Particulate Saline Slurries," and U.S. patent application Ser. No. 09/632,195, filed Aug. 2, 2000, by Lance B. Becker, Terry Vanden Hoek, and Kenneth E. Kasza, entitled "Method For Inducing Hypothermia," all of which are incorporated herein by reference in their entirety.

Phase-change ice slurries have been used for cooling in large building complexes. The use of slurries for cooling buildings has shown that ice particles suspended in water, if engineered to have the correct characteristics, can be pumped as readily as water and are stable for significant periods of time without agglomeration. The cooling capacity of such a slurry can be 5 to 10 times that of an equal mass of water which exhibits only sensible heat cooling capacity, as opposed to heat of fusion effects.

For use in cooling buildings, the particles preferably are small relative to the conduit diameter, not loaded to a level of more than 30% ice in order to enhance delivery to the target cooling zone, and relatively smooth to avoid particle entanglement and formation of large clusters. Small additions of chemical adjuvants to a slurry, such as freezing point depressants, have been shown to dramatically improve the fluidity and storability of the slurry by altering the microscale features of the individual particles comprising the slurry.

For background information on phase-change slurries, and specifically ice slurries, see Kasza, K. E., and Chen, M. M., Assessment of impact of advanced energy transmission fluids on district heating and cooling systems (phase I), *Argonne National Laboratory,* 1987; Kasza, K. E., and Chen, M. M., Improvement of the performance of solar energy and waste heat utilization systems by using phase-change slurry as an enhanced heat-transfer storage fluid, *ASME J. Solar ENG.* 107: 229-236, 1985; Kasza, K. E., and Hayashi, K., Ice slurry cooling research: Storage Tank Ice Agglomeration and Extraction, *ASHRAE Transactions Annual Meeting,* Seattle, Wash., June 1999; Liu, K. V., Choi, U.S., and Kasza, K. E., Pressure drop and heat transfer characteristics of particulate slurry channel flows, *ASME FED* Vol. 75, 1988; and Hayashi, K., and Kasza, K. E., A method for measuring ice slurry particle agglomeration in storage tanks, *ASHRAE Presentation Winter Meeting,* 1999. Each of the references above are incorporated herein by reference in their entirety.

For human use, ice, with its large heat of fusion (80 cal/gm) is a good candidate for the basis of phase-change slurries. For example, a 50/50 mixture of ice and water furnishes nearly 10 times the cooling capacity as an equal mass of water at 0° C. containing no ice. One example of a slurry suitable for use in humans is about a 0.9% saline (sodium chloride) phase-change ice slurry which has a temperature of −0.3° C. The sodium chloride serves as a freezing point depressant, and the slurry has a temperature and a salt concentration that are compatible with human or other animal tissue. Such a slurry may also be described as containing medical grade sodium chloride (i.e. a medical grade saline solution) with ice particles. The term medical grade is well known in the art to describe compatibility with the tissue at issue (for example, a medical grade sodium chloride saline solution for the human body comprises 0.5% to 6.0%, preferably 0.9%, sodium chloride by weight).

Other slurry examples, although not exhaustive, include sugar-based or sucrose-based aqueous solutions or solutions containing biological antifreeze chemicals. The various additives to water can also be used in different combinations to engineer a slurry having altered medical attributes. A slurry can be used as a vehicle to administer other drugs or biologically active compounds at the earliest stages of treatment for purposes in addition to cooling the patient. Such biologically active compounds include, for example, anti-oxidants and anti-apoptosis proteins.

The phase-change particulate slurries of the present invention are generally characterized by their high cooling capacity, fluidity, stability, and compatibility with human tissue. Preferably, the slurries have a transition temperature (freezing and melting point) that does not cause tissue damage.

The saline ice slurries according to the present invention preferably contain sodium chloride concentration in the range of about 0.5% to 6.0% (inclusive of both the liquid in the solution and the ice particles). The loadings, or percentage of ice crystals, are preferably in the range of about 5% to 74%. Although any range of loading may be used, for example, about 30% or about 40% loading, it is more preferable to highly load the slurries with a concentration of ice particles of about 50% or greater. A slurry loaded with the maximum amount of ice particles is desirable as the cooling rate increases with an increase in the ratio of ice particles to solution. The percentage 74% above is maximum overall percentage of ice particles in a solution as it is the maximum theoretical percentage of ice particles in a solution (hexagonal close packed structure). As above, for internal delivery to a target cooling zone, the particle size may be small relative to the diameter of the delivery system (e.g. endotracheal tube to the lungs) to enhance delivery to the target cooling zone and relatively smooth.

EXAMPLE 1

The first example is an ice slurry made from medical grade sodium chloride saline solution. This slurry is used to cool major blood vessels which flow to the head and the heart as with the aortic flush and neck injections described above. The movement of the slurry and the transport of cooled blood into the critical zones is enhanced by chest compressions.

Figure 2:
FIG. 2. Large 3 to 25 mm entangled ice crystals formed in a beaker of pure water.

The sodium chloride in aqueous solution serves as a freezing point depressant and alters the nature of the ice crystals formed in solution when the solution is cooled to its freezing point. Using about a 0.9% saline solution, a slurry is formed in a saline solution confined in a container or in a saline solution directly in a plastic medical injection bag ensuring sterility for the patient and convenience for the suppler. The solution is cooled to the point where ice crystals form. The freezing point for a 0.9% concentration, for example, of sodium chloride is −0.3° C. In contrast to pure water, the saline solution in the beaker and the medical injection bag forms very small separated ice crystals of a size less than 0.1 mm initially. These very small ice crystals grow to approximately 0.2 or 0.3 mm as the ice crystal loading grows with time after initial nucleation of the solution and are typically no more than about 1 mm in size. The slurry is allowed to further increase in ice crystal concentration for about 15 minutes, yielding an ice crystal concentration of approximately 15 to 20%. The ice particles are quite smooth due to the presence of the sodium chloride. At this concentration of ice crystals, the mixture remains very fluid and syrupy in texture. FIG. 1 shows the saline slurry created in the beaker. This slurry readily flows through 3 mm diameter tubing. FIG. 2 shows the larger 3 to 25 mm entangled ice crystals formed in a beaker of pure water.

Figure 3A:
FIG. 3a. Microscopic view of a pure water slurry.
Figure 3B:
FIG. 3b. Microscopic view of a 0.9% sodium chloride aqueous solution slurry.

FIGS. 3*a* and 3*b* show pure water and saline slurries, respectively, viewed under a long range microscope. In the sodium chloride solution, the small individual crystals are quite smooth. In the pure water slurry, the crystals are rough. The saline slurry, therefore, is quite fluid compared to the pure water slurry which has very large dendritic-type crystals.

Saline ice slurries, and other suitable slurries of the present invention, are made using several different approaches. One approach is a batch approach in which beakers of solution or plastic IV bags containing saline solution are immersed in a recirculating water bath chiller. The solutions are cooled until a slurry is formed. A second approach uses a significantly modified commercially available continuous flow ice particle generator and particle concentrator/accumulator (for time of need production) to generate a slurry.

Preferably, the commercially available continuous flow ice particle generator and particle concentrator/accumulator are reduced in size to be compatible with medical needs and new control features are implemented to allow generation and storage of ice particles suitable for medical use. Equipment for feeding the slurry to the medical delivery devices is also designed into existing slurry generators. The equipment is also designed to eliminate the potential of slurry contamination.

Preferably, a stable (storable), fluid and highly loaded (50% or greater) ice particle slurry with medical grade saline solution is produced. An example of the rapidity of cooling may be seen from a slurry with 50% ice particles, which has 10 times the cooling capacity of saline solution without particles. The characteristics of slurries are strongly dependent on: the temporal and thermodynamic pathways under which the slurries are formed; the concentration of the sodium chloride in the aqueous solution; the actual cooling equipment used; and the presence of other trace chemicals or impurities which act as ice crystal nucleation sites. The slurries preferably have a transition temperature (melting point) that does not cause tissue damage.

It is known that slurry flowability also depends on loading, surface roughness, and particle size. Preferably, a stable saline slurry of the maximum loading (maximum cooling capacity) and the flowability necessary for tubing delivery and flow in blood vessels is produced.

To determine the influence of the various parameters which influence slurry characteristics, batches of saline ice slurry for several sodium chloride concentrations in the range about 0.5 to 6.0% using 2 different approaches are generated. The first consists of the batch approach involving containers of solution or plastic IV saline bags immersed in a recirculating water bath chiller. The second approach is to modify a commercially available continuous flow ice particle generator and particle concentrator/accumulator (time of need production) and to generate a slurry. These two approaches allow evaluation of different production methods and allow evaluation of the influence of production devices on slurry characteristics. For both devices various cool-down rates, temperature hold conditions, and storage periods are imposed on the slurries during formation and storage to assess the influence on slurry characteristics.

The slurry flowability through plastic tubing in the size range about 1 to 6 mm diameter is evaluated for tubing having a length in the range of about 0.3 to 2 m for both methods of slurry production, various loadings in the range 5 to 74%, and for the various saline concentrations. Flow is induced both by squeezing plastic IV saline bags and by metered flow pumping at various rates from 10 to 1000 cc/min. Flowability is assessed by visual detection of ice particle blockage aided by microscope and video recording and by measuring any pressure drop over the length of tubing. Because particle size and roughness strongly influence slurry behavior, these characteristics are quantified using the microscope/video images of slurry. Slurry storability is evaluated by storing the slurry for various time periods and checking its flowability.

EXAMPLE 2

In another embodiment, cooling of the heart is achieved by charging the lungs with a phase-change slurry. Due to the almost intimate contact of the lungs with one side of the heart, charging the lungs greatly improves the rate of cooling of the heart. One example of a phase-change ice slurry used for the lungs is in the form of liquid perfluorocarbon or sodium chloride solution either which may be used as the carrier of ice particles into the lungs. When oxygenated, the sodium chloride solution or perfluorocarbon liquid can also serve as a liquid ventilator or oxygen transporter.

During cardiac arrest, the lungs are effectively a dead air space and behave as an insulating layer that significantly reduces heat transfer to and from the heart, impeding cooling applied externally to the chest. Because the heart lies immediately behind the lungs, with only a thin membrane layer separating the two regions, the heart can be more rapidly cooled by using a coolant delivered to the lungs to supplement external cooling. The coolant to the lungs can be administered to a patient through a tube extending into the lungs as part of a modified breathing apparatus or by direct tube feed from the slurry producing equipment.

Among their unique properties, perfluorocarbon liquids are immiscible with water, very chemically and biologically inert, and have an extraordinary capacity for dissolving oxygen. The ice particle perfluorocarbon liquid slurry is formed by cooling an emulsion of saline solution (or other suitable liquid) and sodium chloride solution or perfluorocarbon liquid to create a slurry. To oxygenate such a perfluorocarbon slurry or a saline ice slurry, microbubbles of oxygen may be infused into the slurry by forcing oxygen through a micropore porous stone. The micropore porous stone forms microbubbles that are incorporated/entrained into the slurry by mixing them in as a gaseous third phase in the mixing apparatus. The oxygen may also be introduced into the slurry just prior to using the slurry by imbedding the micropore porous stone into the delivery line to the body, thereby allowing careful metering of the delivered oxygen.

In one example, the ice slurry was made by emulsifying saline solution (0.9% or higher concentration) in perfluorocarbon liquid in a container and then batch chilling the mixture to the freezing point. The freezing point for this mixture was 0° C. and the slurry was loaded with about 15% ice particles. The slurry of about 15% ice particle loading was quite fluid and the particles were quite smooth, thereby permitting easy flow along the delivery lines.

The initial relative proportions of the constituents dictate the ice particle slurry concentration. It is known that slurry flowability also depends on loading, surface roughness, and particle size. Preferably, a stable saline/perfluorocarbon slurry of the maximum loading (maximum cooling capacity) and the flowability necessary for tubing delivery into the lungs is produced. Saline solution concentrations are preferably in the range of about 0.5 to 6.0% and ice particle loading is preferably in the range of about 5 to 74%.

There are several different methods of combining the liquids. The saline solution, prior to freezing the mixture, is broken into very small droplets suspended in the immiscible perfluorocarbon liquid. The size of the saline solution droplets prior to freezing determines the slurry ice particle size after freezing. The formation of small smooth ice particles enhances slurry flowability.

One approach for forming the small saline solution droplets involves mechanically mixing the constituents in a beaker with a variable speed mixer. The more intense and longer the duration of the mixing, the smaller the droplets. A second method consists of using an ultrasonic mixer to achieve small saline solution droplet sizes. The ultrasonic approach is preferred because it allows the use of closed sterilized containers of the desired mixture without concerns of contamination. The mixing energy is transferred through the walls of the container. In both cases, the containers of mixed solutions are batch cooled to the ice particle formation temperature by immersion in a recirculating bath chiller or other suitable cooling device. The slurry can also be made in a continuous process device for on-demand delivery.

Preferably, stable (storable), fluid, and highly loaded (50% or greater) ice-particle slurry with medical grade saline/perfluorocarbon liquids for pulmonary cooling is produced. These desired slurry characteristics, just as in the case of saline slurries, are strongly dependent on: the temporal and thermodynamic pathways under which the slurries are formed; the concentration of the slurry constituents; the actual cooling equipment used; and the presence of other trace chemicals or impurities which act as ice crystal nucleation sites. Furthermore, the slurries preferably have a transition temperature (melting point) that does not cause tissue damage.

To determine the effect of the various parameters which influence slurry characteristics, batches of saline/perfluorocarbon ice slurry for several emulsified/highly mixed mixtures of saline solution concentrations in the range of 0 to 6.0%, for various loading concentrations in the range of 5 to 74%, using the different methods of combining the liquids, are produced.

These two approaches to the production of the saline/perfluorocarbon ice slurry allow evaluation of different production methods and allow evaluation of the influence of the production device on the slurry characteristics. For both slurry preparation methods, various cool-down rates, temperature hold conditions, and storage periods are imposed on the slurries during formation and storage to assess the influence on slurry characteristics.

The slurry flowability through plastic tubing in the size range of 4 to 12 mm diameter is evaluated for tubing in the length range of 0.3 to 1 m for both methods of slurry production, various loadings in the range 5 to 74%, and for the various saline concentrations. Flow is induced both by squeezing a plastic flexible container such as those similar to ventilating bag-valve systems and by metered flow pumping at various rates from 200 to 1000 cc/min. Flowability is assessed by visual detection of ice particle blockage aided by microscope and video recording and by measuring pressure drop over the length of tubing. Because particle size and roughness strongly influence slurry behavior, these characteristics are quantified using the microscope/video images of slurry. Slurry storability is evaluated by storing the slurry for various time periods and checking its flowability. Preferably, a slurry with large cooling capacity, sufficient fluidity, and stability is produced.

Equipment for Making Slurry

The equipment for generation of each type of slurry may involve either batch processing in a chilled bath or the use of a significantly modified commercially available continuous flow ice particle generator and particle concentrator/accumulator (time of need production) to allow generation of slurry characteristics suitable for medical use in a continuous on-demand basis.

Ice slurry generation and storage equipment and the protocols for using them should be compatible with patient use. Preferably, the equipment design allows cooling devices which provide an optimum slurry with large cooling capacity, sufficient fluidity, and stability under the conditions and use scenarios needed for out-of-hospital treatment.

Cell Data

The focus of resuscitation treatment for ischemic diseases involving impairment of blood flow and reduced oxygen flow to tissues, including stroke, myocardial infarction, hemorrhagic shock, and cardiac arrest, has been to shorten the time of ischemia, and reperfuse at normal physiologic conditions as quickly as possible. However, recent data suggest that altering the conditions within the first minutes of reperfusion may be even more important than shortening the time of ischemia.

Figure 4:
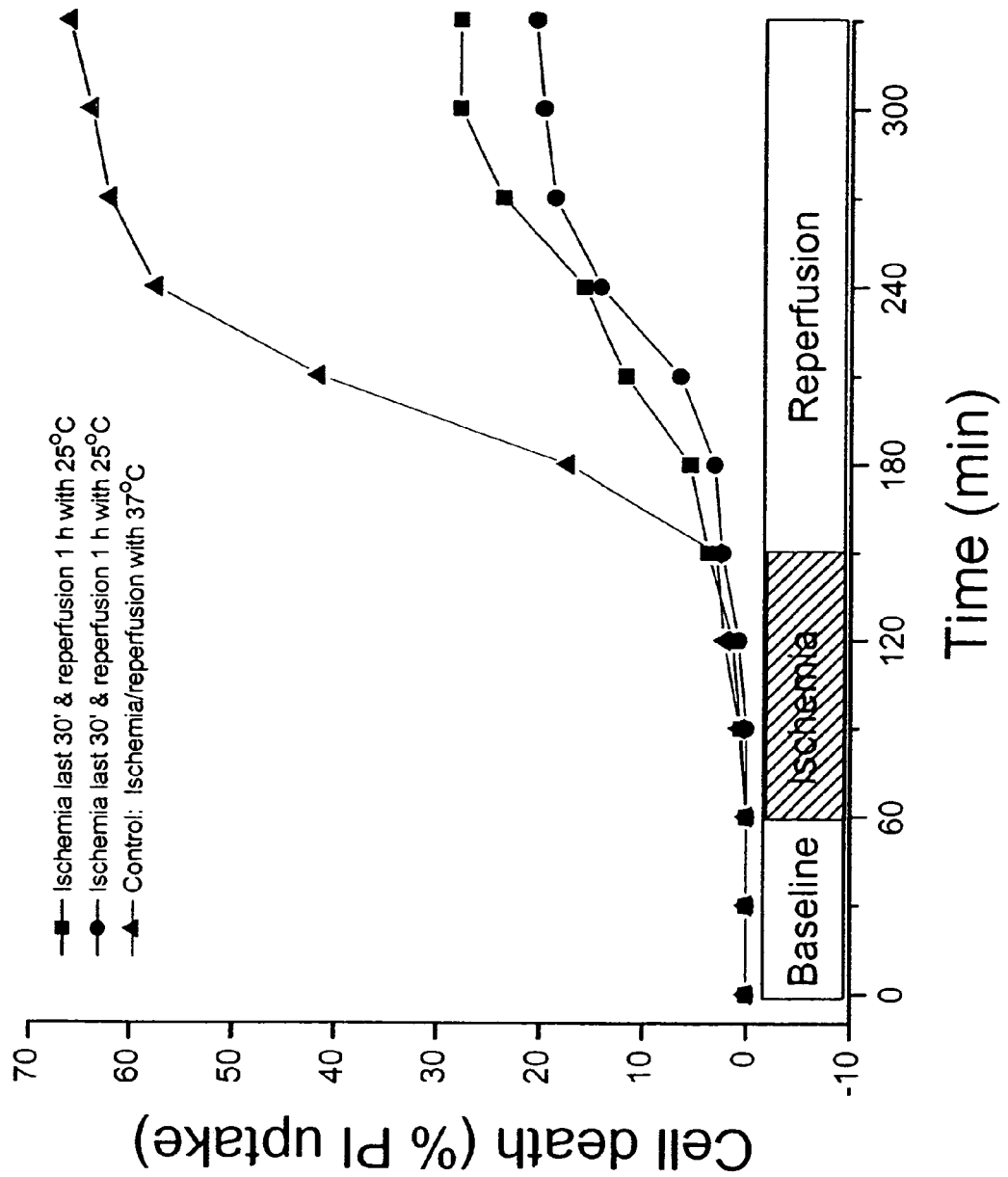
FIG. 4. Cell death versus time.

Studies on the rapid induction of hypothermia prior to the time of reperfusion indicate that lengthening the time of ischemia from 60 to 70 minutes improves outcome when the additional time of ischemia was used to induce hypothermia. As seen in FIG. 4, if cardiac cells exposed to normothermic (37° C.) ischemia for 60 minutes are made ischemic for an additional 30 minutes at 25° C. (90 minutes total without oxygen), and reperfused at 25° C. for an additional 60 minutes before being warmed back to 37° C., their rate of cell death Oust over 20% cell death) is significantly better than if cells were exposed to ischemia for 60 minutes at 37° C. and reperfused immediately with normal physiologic solution (i.e., at 37° C.)—resulting in almost 50% cell death. Control cells made ischemic for 90 minutes at normothermic conditions had over 60% cell death. Thus, shortening the time of ischemia may be less important than ensuring that ischemic cells are hypothermic at the time of reperfusion.

The implications are that total body cooling for cardiac arrest, and selected organ cooling of the heart and brain for myocardial infarction and stroke respectively, can significantly open the window of opportunity to save these organs from ischemia/reperfusion injury by giving physicians more time to treat the patient. For example, for stroke patients, the current time window in which physicians can safely administer thrombolytics to dissolve blood clots and reperfuse ischemic regions of the brain is 3 hours, far too little time for most patients to benefit from this therapy. These results indicate that, if cooled prior to reperfusion (i.e., prior to the time of administering thrombolytic drugs), as with the pericarotid cooling technique, the time window of opportunity to reperfuse would be extended well beyond 3 hours.

Models

A simplified spherical text book classical multilayer heat conduction model, with and without an internal heat sink, has been implemented to analyze cooling of the head and the heart. The model is found in Carslaw, H. S. and Jaeger, J. C., *Conduction of Heat In Solids*, Oxford University Press, 1973, pp. 233-237, which is incorporated herein by reference. For the head, the sphere model has four layers. The heart is modeled as a single element sphere. Both the head and heart are modeled with and without an internal heat sink. The heat sink allows simulation of internal organ cooling resulting from the cooler blood entering induced by chest compressions. To verify the accuracy of the simplified model, cooling data on the cooling rate associated with a ham suddenly immersed in a ice slush bath is compared with model predictions. The following summarizes the results from the ham, head, and heart cooling assessments.

EXPERIMENTS

Heat transfer Modeling Results: Examples 3-6

EXAMPLE 3

Ham: Surface Cooling/no Blood Flow

As a means of obtaining an indication of a cool-down rate associated with external surface cooling only of a large tissue mass of size and surface area similar to the head, an experiment was conducted on a 9.8 pound ham (shank portion) with an imbedded bone mass. The ham was cooled down from an initial temperature of 29.4° C. to 16.7° C. in 30 minutes by direct full immersion in a tightly packed ice slush water bath at 0° C. with a thermocouple imbedded 3.5 inches into the thickest part of the ham. The resulting core cool-down rate was 0.42° C./min. These results confirm that surface cooling only, in the absence of blood flow, falls far short of achieving the desired cooling.

Figure 5:
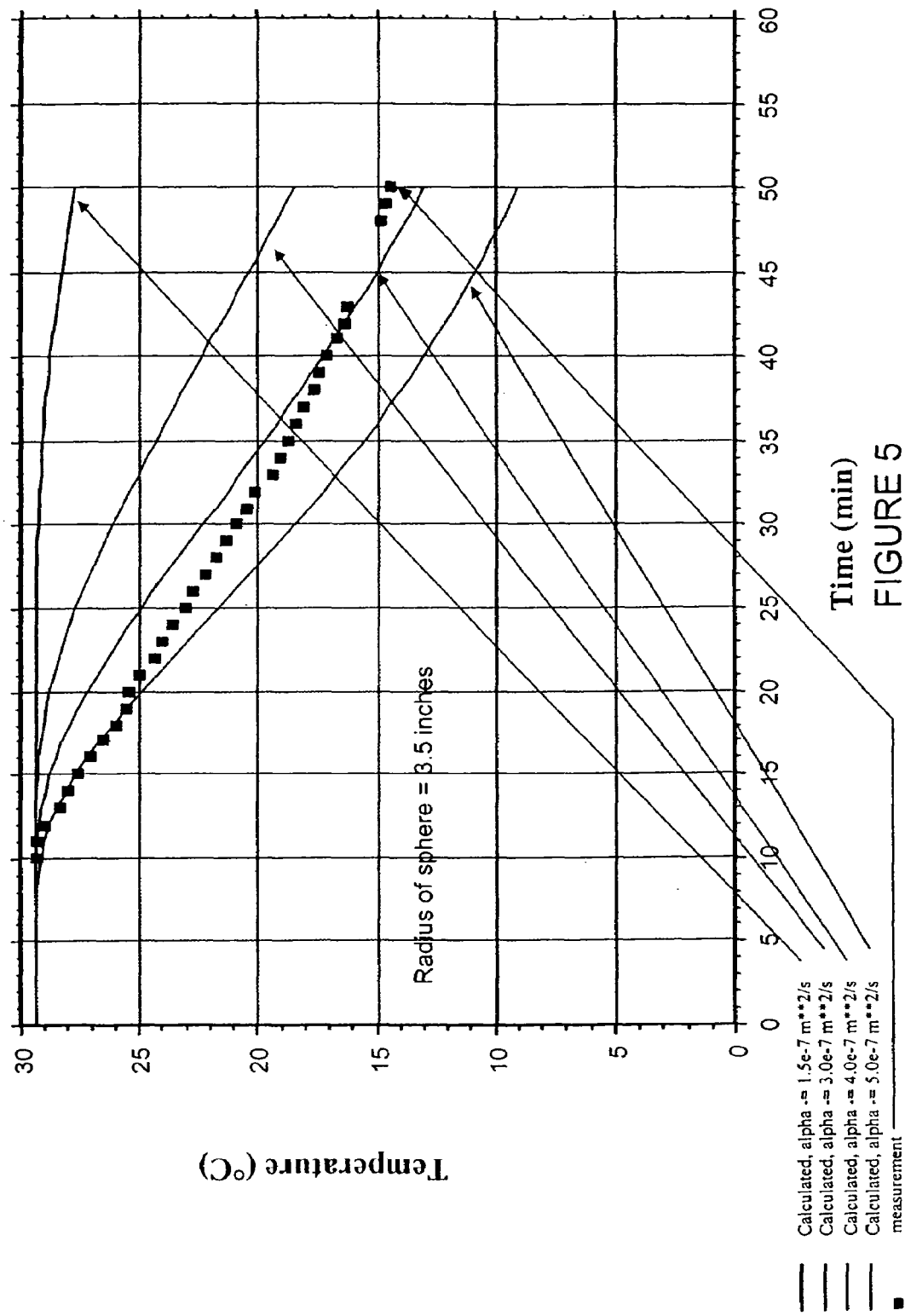
FIG. 5. Predicted versus measured core temperature for a ham suddenly immersed in ice slush.

FIG. 5 shows the results of the sphere heat conduction model applied to the ham compared with the measured ham core temperature history based on a sphere of radius b=3.5 inches for thermal diffusivities ranging from 1.5 to $5.0 \times 10^{-7}$ m²/s.

EXAMPLE 4

Head Model

Figure 6:
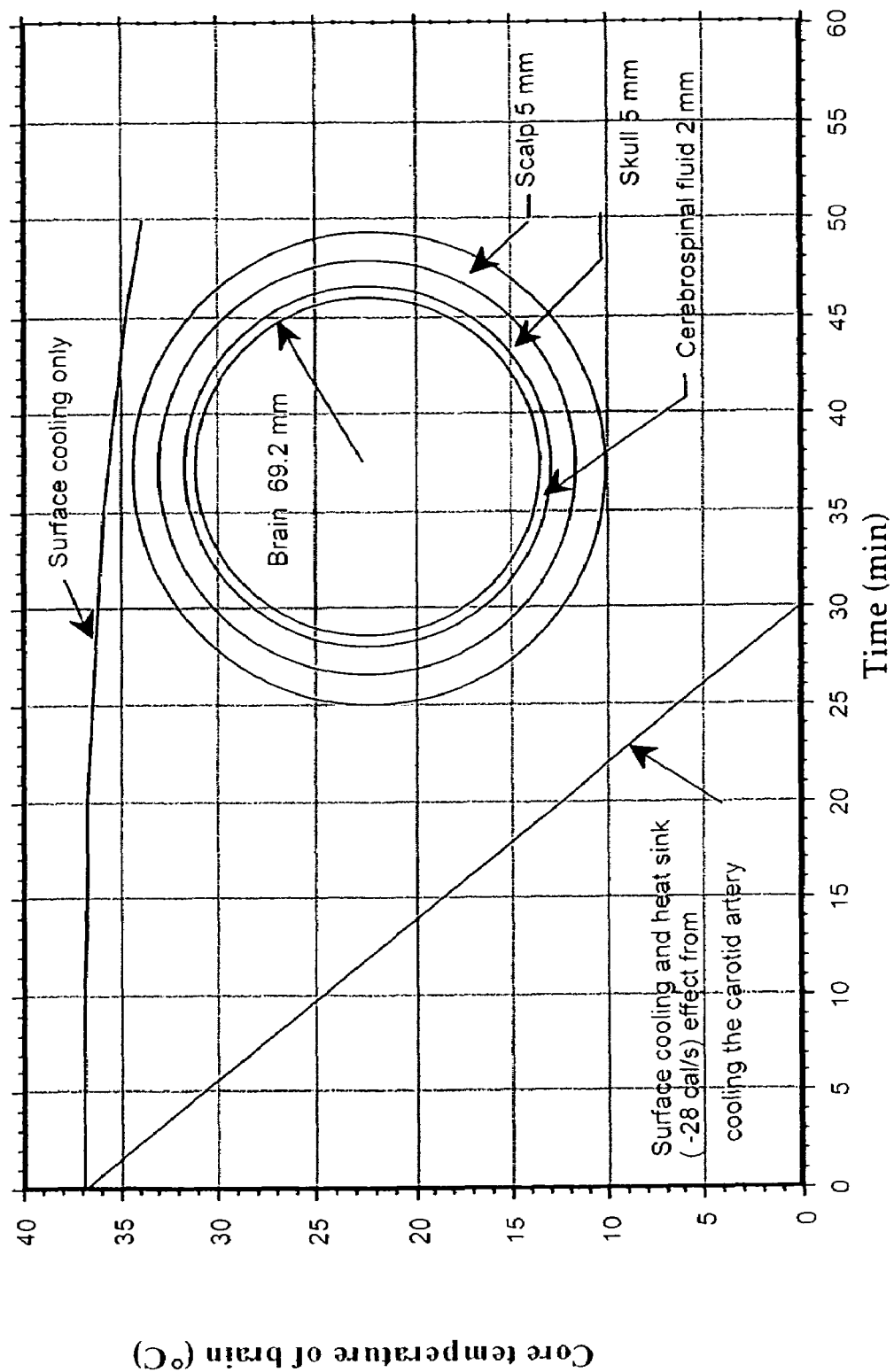
FIG. 6. Transient temperature at the brain core. Head initially at 37° C. subjected to a sudden immersion in an ice bath at 0° C. Depicts influence of surface cooling only and combined effect of surface and internal cooling by cooled carotid blood flow into brain.

Models for brain core temperature using external surface cooling alone and for the combined effect of external and internal pericarotid cooling are presented in FIG. 6.

The external surface cooled model of the head/brain has the following features. The head is modeled as a 4-layered sphere with heat conduction to an ice slurry bath at 0° C. upon sudden immersion. The 4 layers of the sphere from the outer to the inner zones are the scalp, the skull, the cerebrospinal fluid (CSF), and the brain, respectively, as shown in FIG. 6. The mass of the brain considered is 1500 g which is equivalent to a volume of 1388 cm³ and a radius of 69.2 mm. The thickness of the scalp, the skull, and the CSF are 5 mm, 5 mm, and 2 mm, respectively. The radius of the brain is divided into 10 equal partitions. The governing classical heat conduction equation was discretized into the finite difference form and solved numerically for temperature. The equation used is $a_i T_i = b_i T_{i+1} + c_i T_{i-1} + d_i$ where i represents the number of partitions. The equations were solved by the Tri-Diagonal-Matrix Algorithm. (See S. V. Patanker, *Numerical Heat Transfer and Fluid Flow* (*Hemisphere Series on Computational Methods in Mechanics and Thermal Science*), Hemisphere Publishing, pp. 52-54, 1980. See also Carslaw, H. S. and Jaeger, J. C., *Conduction of Heat In Solids*, Oxford University Press, 1973, pp. 233-237.)

FIG. 6 shows the transient temperature at the center of the brain. The cooling time of the center of the brain from 37° C. to 25° C. is 93 minutes. The brain core cools very slowly. However, the brain outer edge sees protective temperatures of 25° C. at 10 minutes into the cool down. The head model indicates that the rate of cooling of the brain is improved significantly by utilization of internal pericarotid blood cooling in conjunction with the external cooling.

The heat transfer to the carotid artery has been modeled and the resulting cooling capacity of the blood flowing into the brain resulting from chest compressions is used to evaluate whether the cooling capacity needed in the brain in the form of a distributed heat sink could be achieved. The carotid artery on each side of the neck is assumed to have the following characteristics: diameter=1.2 cm; length=10 cm; blood flow rate from chest compressions=125 cc/min; and surface temperature due to ice slurry=0° C.

The analysis of the carotid artery shows that at the beginning of the cooling process, the blood enters the 10 cm effective cooling length of artery at 37° C. and exits at 24.8° C. 14.8 cal/s are removed from the blood per carotid. As time proceeds, the blood exiting the carotid heat exchanger becomes cooler. Hence, the blood entering the brain also becomes cooler, even at the beginning of the cooling, with a temperature near the desired cool-down cell protection target temperature of 25° C.

The head heat conduction transfer model used for predicting the influence of surface cooling alone is implemented with a uniform heat sink per unit volume represented by $q'''$ for the brain region and the core temperature predicted versus time with both external and internal heat sink cooling modes operating. The value of $q'''$ used is 0.02 cal/s-cm³ which is based on cooling a brain of mass 1500 g, having volume 1388 cm³, and specific heat of 3850 J/kg-° C. from 37° C. to 25° C. in 10 minutes. The average brain cooling rate based on these assumptions is 27.6 cal/s. As shown in FIG. 6, the addition of the internal brain cooling resulting from cooling of the carotid blood flowing into the brain furnishes a significant improvement in cooling over the case of external cooling alone. The brain core temperature reaches 25° C. in 10 minutes and, most importantly, the internal heat sink effect is obtainable from the carotid cooling.

Heart Model

The cool blood entering the heart is modeled, as for the brain, as a uniformly distributed heat sink. The effectiveness of these cooling methods are discussed below for two simulated cases (EXAMPLE 5 and EXAMPLE 6). The spherical heart heat conduction transfer model assumes a heart mass of 400 g, a volume of 370 cm³, and a radius of 44.6 mm.

EXAMPLE 5

Heart Model Case 1: Pulmonary cooling with no blood flow, no chest compressions, lungs filled with ice slurry, and trunk packed in ice.

This case calculates the heart core cool-down rate associated with the scenario of the lungs being filled with ice slurry at 0° C. at time zero and the heart separated by only a thin tissue layer (2 to 5 mm thick) from the lungs with the heart initially at 37° C. The trunk is subjected to an ice bath. Chest compressions which would induce blood flow are not used. The lungs could hold 3 or 4 liters of ice slurry in a single charge and the slurry contains approximately 30% by volume of ice particles (ice has a heat of fusion of 80 cal/g or 144 Btu/lb.). This analysis, in addition to predicting heart cooling rate, also yields an estimate of how much cooling it takes to cool the heart from its initial uniform temperature of 37° C. to a target core temperature of 25° C. This estimate also provides information on how much ice slurry is needed to charge the lungs to achieve the target cool down.

Figure 7:
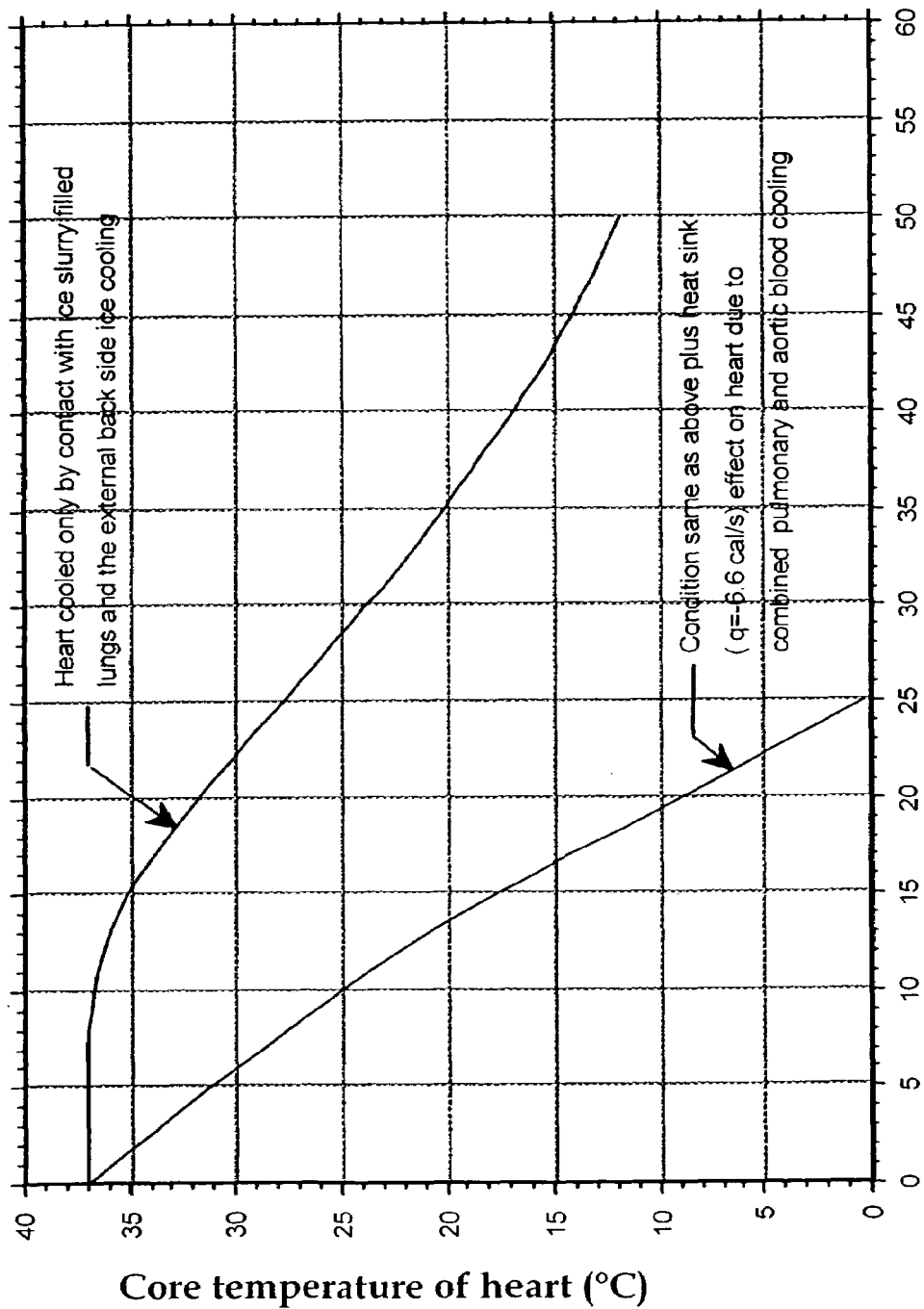
FIG. 7. Transient temperature at the center of a spherical heart model of mass 400 g and initial temperature of 37° C. for 2 modes of cooling.

In this model, it is assumed that the surface of the heart is 100% in contact with the lungs and maintained at 0° C. surface temperature resulting from the injection of the ice slurry into the lungs and the trunk in an ice bath. The transient temperature at the heart core is shown in FIG. 7. It takes about 28.4 minutes to cool from 37° C. to 25° C. This is longer than the target time of 10 minutes. For the present case, the amount of heat loss from 37° C. to 25° C. is calculated to be 38.8 Btu, which is equivalent to the latent heat of 0.27 lbs. of ice. For a 30% ice particle loaded slurry charged into the lungs of 3 to 4 liters capacity, a single charge would place over 2 lbs. of ice in the lungs which is adequate to achieve cooling, but as above, not optimal.

EXAMPLE 6

Heart Model Case 2: Combined pulmonary cooling with blood flow.

In this case, the full combination of cooling modes is considered. That is, the heart is cooled down through the conductive heat transfer due to the contact between the slurry filled lungs and the heart (see Heart Model Case 1, EXAMPLE 5), and cooling due to cooler blood flowing through the heart. The heart is cooled as a result of the combination of the injection of ice slurry into the aorta, cooled jugular blood, and blood cooled in the lungs flowing into the heart as a result of chest compressions in the absence of a naturally pumping heart.

To simulate internal cooling, a uniformly distributed heat sink, $q'''$, in the heart sphere model is used to represent the convective heat transfer between the heart and the blood flow. The heart core temperature for $q'''=0.018$ cal/s-cm$^3$ which corresponds to an energy removal rate of $-6.63$ cal/s is shown in FIG. 7. The appropriate value of $q'''$ is determined in the same way as for the brain calculations. Significant improvement is obtained with the cooled blood flow over Heart Model Case 1, EXAMPLE 5. From FIG. 7, it is noted that the cooling time from 37° C. to 25° C. at the center of the heart under the condition of no blood flow contribution, i.e. $q'''=0$ is 28.4 min, the result from Heart Model Case 1, EXAMPLE 5. However, the cooling time is reduced to 10 minutes for the volumetric heat sink value of 0.018 cal/s-cm$^3$ applied to the heart. The two cases show that the cooled blood flow is very important for cooling the heart core quickly following cardiac arrest. This cooling by blood flow is achieved with the use of internal ice slurry cooling.

These scoping models are based on simplified spherical geometry and lumped parameter textbook classical heat conduction heat transfer model approximations. (Carslaw, H. S. and Jaeger, J. C., *Conduction of Heat In Solids*, Oxford University Press, 1973, pp. 233-237.)

The cooling model studies of the brain and heart regions yield numerical models that are used to develop and evaluate the various cooling approaches. The initial target is a cool-down from 37° C. to 25° C. in 10 minutes.

Scoping assessments of cooling rates are used to evaluate combined external and internal cooling for the lungs and heart. A first cut model of the heart cool-down rate with the lungs filled with ice slurry at 0° C. at time zero and the heart separated by only a thin tissue layer (2 to 5 mm thick) from the lungs with the heart initially at 37° C. has been developed. This analysis, in addition to predicting heart cooling rate, also yielded an estimate of how much ice slurry it would take to cool the heart from its initial uniform temperature of 37° C. to a center temperature of 25° C.

These scoping models are based on simplified spherical geometry and lumped parameter approximations. Additional heat transfer models are developed based on finite element representations of the complex geometries, the boundary conditions, and the material property variations of the various body elements involved. The commercial code PROSTAR (pre-processor of STAR-CD Code) is used to generate the computational meshes to more accurately represent the actual geometry of head and heart and represent spatial variations in the applied boundary conditions and tissue properties.

EXAMPLE 7

In this study, the ability of a phase-change ice slurry to provide targeted cooling of the heart and brain when delivered intravenously, and through an endotracheal tube into the pulmonary space during cardiac arrest with chest compressions in a swine model of cardiac arrest was tested.

Phase-Change Ice Slurry

The slurry used for these experiments was a saline based ice slurry which consisted of 30% ice generated from a 0.9% saline solution. Ice particle size was less than 0.1 mm (measured microscopically); flowability through IV tubing was good; and the slurry did not degrade after 4 hours storage. The temperature of saline ice slurry produced was −0.3° C., a temperature that is well tolerated by biological tissue. Other similar experiments have been performed with a saline based ice slurry having over 40% and 50% by weight of ice particle loading.

Animal Instrumentation

The use of swine as a model of cardiac arrest has been well described in the literature. (See, for example, Idris, A. H., Wenzel, V., Becker, L. B., Banner, M. J., Orban, D. J., Does hypoxia or hypercarbia independently affect resuscitation from cardiac arrest?, *Chest*, 108(2): 522-28 (1995); Idris, A. H., Becker, L. B., Fuerst, R. S., Wenzel, V., Rush, W. J., Melker, R. J., Orban, D. J., Effect of ventilation on resuscitation in an animal model of cardiac arrest, *Circulation*, 90(6): 3063-69 (1994); and Swindle, M. M., The use of animals in surgical research, *J Invest Surg.*, 1(1): 3-4 (1988)).

Domestic swine weighing 30-40 kg were intubated with a #7 endotracheal tube, following anesthetic induction with ketamine (20 mg/kg IM). Animals were placed in the dorsal recumbent position. Anesthesia was maintained with isofluorane inhalant gas and 100% oxygen. Vital signs were continually monitored and anesthetic levels were adjusted to maintain physiologic homeostasis and absolute absence of discomfort. Animals were ventilated with a time-cycled, pressure-controlled electronic ventilator to maintain an end-tidal $CO_2$ of 35-45 torr.

Normal saline solution was administered at a rate of 10 cc/kg/hr, through a 22 g intravenous catheter placed in the auricular vein. A cut down was performed in the area of the femoral triangle to allow placement of a longdwelling catheter into the femoral artery. To place needle temperature probes in the brain, a 2 cm incision was made through the skin overlying the skull. A bone drill was positioned through the skin incision, and a 4 mm hole was placed through the skull just above the orbital rim. The dura was visualized and penetrated with a needle thermistor probe inserted to the frontal lobe to a depth of 4 cm. The procedure was repeated on the other side for bilateral temperature monitoring. Baseline temperatures were taken from all sites. During chest compressions, continuous temperature measurements were taken from the right and left brain, esophageal, and rectal probes. Immediately following termination of the experiment, heart temperature was measured via direct insertion of a needle probe into the muscle of the left ventricle.

A compression cylinder (Thumper, Michigan Instruments) was positioned over the sternum with the compression pad centered at the midsternum to provide 80 compressions per minute at a compression depth of 3-4 cm. The device is tested prior to induction of cardiac arrest to confirm the presence of an adequate arterial waveform during "thumping."

Experimental Protocol

Cardiac arrest was induced by intravenous injection of 5 cc's of saturated KCl, and confirmed by the complete absence of EKG waveform and blood pressure. Upon death, CPR was begun and slurry was administered. Ice slurry was delivered down a 5 French tube inserted into the lumen of the endotracheal tube, until slurry overflowed the endotracheal tube. The animal was simultaneously ventilated through the endotracheal tube using a 3 L ventilation bag, such as an "Ambu" bag and ventilations were performed at a rate of one ventilation per 5 compressions. At approximately 2-minute intervals, the previously instilled ice slurry was removed and replaced with approximately 100-150 cc of fresh slurry. In the experiment adding ice slurry to the venous system, approximately 1500 cc ice slurry was additionally administered via the femoral venous line. CPR and slurry administration were continued until the brain temperature decreased from baseline (approximately 38° C.) to approximately 30° C. A thoracotomy was performed and three temperatures were taken under direct visualization from the anterior ventricular wall at a depth of about 0.5-1.0 cm.

Data Analysis

Simple descriptive statistics are used for temperature data. Temperature was recorded each minute for 30-40 minutes and data points were collected for each site per animal. Two-tailed t-tests were performed as tests of significance, with $p<0.05$ considered to be significant.

Results

Pulmonary Cooling Only

The results are presented in Table 1. Over the 40 minutes of cardiac arrest with chest compressions and pulmonary cooling, rectal temperature decreased by 1.1° C., while brain temperature decreased by 6.3° C., and heart temperature by 14° C. More frequent instillation of ice slurry produced more rapid cooling with a maximal cooling rate sustained over 10 minutes of −2.8° C. (per 10 min). An additional temperature probe in the esophagus showed similar or cooler temperatures to those in the heart (data not shown).

EXAMPLE 8

Combined Pulmonary and Intravenous Slurry Administration

An experiment was performed with pulmonary cooling as above, but in addition, there was direct injection of ice slurry into the femoral venous line. Approximately 1500 cc of ice slurry was injected over 30 minutes via a catheter. As seen in Table 1, cooling rates with additional venous ice slurry appear faster than with pulmonary cooling alone. While rectal temperature decreased by only 1.3° C. over the 30 minute experiment, brain temperature decreased by 8.6° C., and heart temperature decreased by 16° C. Over the best 10 minute cooling period the brain temperature decreased by 5.2° C. A detailed temperature chart for the experiment is seen in Table 1.

Figure 8:
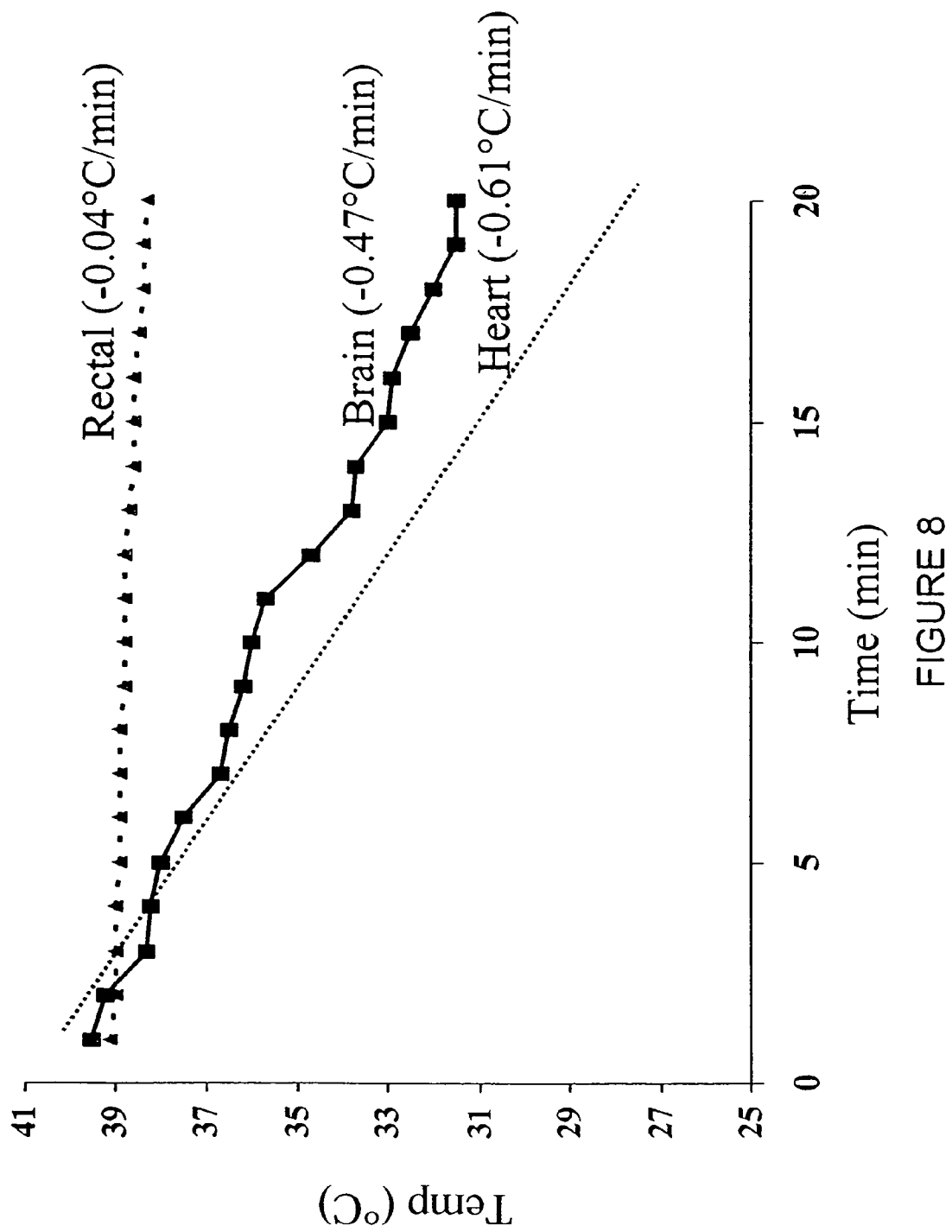
FIG. 8. Combined intravenous and pulmonary cooling during cardiac arrest with chest compressions.
Figure 9:
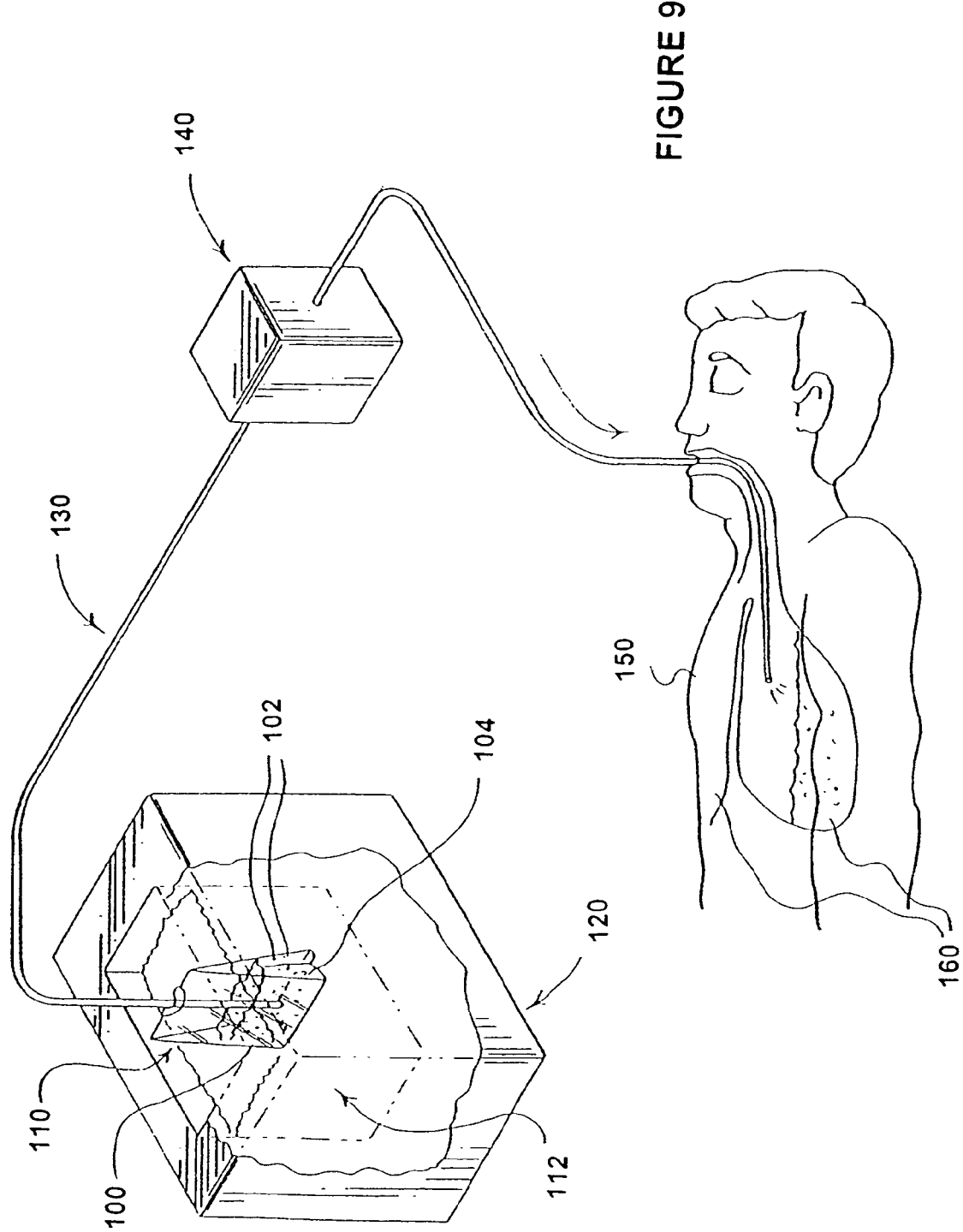
FIG. 9. A schematic view of one exemplary technique.

Data from a single experiment with combined intravenous and pulmonary cooling during cardiac arrest with chest compressions are shown in Table 2 and FIG. 8. Data from a single experiment over time shows heart, brain (average of right and left hemispheres), and rectal temperature over the initial twenty minutes of cooling and cardiac arrest. Note that time zero (0) represents the moment of cardiac arrest, and the heart cooling is averaged (hence, the straight line estimate) over the experiment as it was measured after termination, not continuously.

TABLE 2

Combined intravenous and pulmonary cooling during cardiac arrest with chest compressions

| Site | Cooling Rate per Minute |
|---|---|
| Rectal temperature | −0.04° C./min |
| Brain hemisphere | −0.47° C./min |
| Heart temperature | −0.61° C./min |

Hypothermia was rapidly inducing in a swine model of cardiac arrest using a phase-change ice slurry administered into the pulmonary space and via intravenous catheter. This method rapidly and significantly lowered the temperature of the brain and the heart in these animals during simultaneous chest compressions. Interestingly, the rectal temperature did not appreciably change, consistent with the notion that the technique specifically targeted cooling to the brain and heart. These results are unique and surprising in several respects. First, there are no prior studies, of which the inventors are aware, that document a medical use for internal phase-change slurries for cooling. Second, this is believed to be the first study to identify the lung surface area as a practical system for heat exchange to rapidly cool the brain and heart during CPR. The cooling rates were 10-20 times greater than any other methods available to paramedics in an out-of-hospital setting.

Obviously, numerous modifications and variations of the present invention are possible in light of the above teachings. These teachings serve as examples, and are not to be understood as limiting the scope of the present invention. It is therefore to be understood that the invention may be practiced otherwise than as specifically described herein.

We claim:

1. A method of removing heat from a body comprising:
   administering a phase-change particulate slurry internally to said body; and
   continuing to administer the slurry until a desired amount of heat has been removed from the body.

2. The method of claim 1 wherein the body comprises that of a living animal undergoing treatment.

3. The method of claim 2 wherein the living animal undergoing treatment is a human patient.

TABLE 1

| Site | Average Cooling | Cooling Rate per Minute | Animals |
|---|---|---|---|
| Pulmonary cooling only | | | |
| Rectal temperature | −1.1° C. over 40 min | −0.03 ± 0.006 (SE) ° C./min | (n = 2) |
| Brain hemisphere | −6.3° C. over 40 min | −0.16 ± 0.02° C./min* | (n = 4) |
| Heart temperature | −14° C. over 40 min | −0.35 ± 0.07° C./min* | (n = 2) |
| Best 10 min brain cooling | −2.8° C. over 10 min | −0.28 ± 0.02° C./min | (n = 4) |
| Pulmonary cooling combined with femoral vein ice slurry | | | |
| Rectal temperature | −1.3° C. over 30 min | −0.03 ± 0.007° C./min | (n = 1) |
| Brain hemisphere | −8.6° C. over 30 min | −0.29 ± 0.004° C./min* | (n = 2) |
| Heart temperature | −16° C. over 30 min | −0.53 ± 0.009° C./min* | (n = 1) |
| Best 10 min brain cooling | −5.2° C. over 10 min | −0.52 ± 0.004° C./min | (n = 2) |

*Brain and heart are significantly different from rectal cooling rate ($p < 0.005$)

4. The method of claim 1 wherein the phase-change particulate slurry further comprises a sodium chloride solution.

5. The method of claim 4 wherein the sodium chloride solution further comprises a concentration of sodium chloride between about 0.5% to 6.0%.

6. The method of claim 1 further comprising administering the phase-change particulate slurry to the patient subcutaneously.

7. The method of claim 6 further comprising administering the phase-change particulate slurry into the pericarotid region of the soft tissue of the neck of the patient.

8. The method of claim 1 further comprising administering the phase-change particulate slurry to the patient intravascularly.

9. The method of claim 8 further comprising administering the phase-change particulate slurry into the aorta of the patient.

10. The method of claim 1 further comprising administering the phase-change particulate slurry to the patient intraperitoneally.

11. The method of claim 1 further comprising administering the phase-change particulate slurry into the gastrointestinal tract of the patient.

12. The method of claim 1 wherein the phase-change particulate slurry further comprises a perfluorocarbon liquid.

13. The method of claim 12 further comprising administering the perfluorocarbon phase-change particulate ice slurry into at least one lung of the patient.

14. The method of claim 1 further comprising administering the phase-change particulate ice slurry into at least one lung of the patient.

15. The method of claim 4 further comprising administering the sodium chloride phase-change particulate ice slurry into at least one lung of the patient.

16. The method of claim 4 wherein the sodium chloride solution further comprises a concentration of sodium chloride of about 0.9%.

17. The phase-change particulate slurry of claim 1 wherein the percentage of ice particles in the slurry is between about 5% and 59.5%.

18. The phase-change particulate slurry of claim 4 wherein the percentage of ice particles in the slurry is between about 5% and 59.5%.

19. The phase-change particulate slurry of claim 5 wherein the percentage of ice particles in the slurry is between about 5% and 59.5%.

20. The phase-change particulate slurry of claim 15 wherein the percentage of ice particles in the slurry is between about 5% and 59.5%.

21. The phase-change particulate slurry of claim 16 wherein the percentage of ice particles in the slurry is between about 5% and 59.5%.

22. A phase-change particulate ice slurry for removing heat from a patient comprising a medical grade saline solution and ice particles, the saline concentration being in a range between about 0.5% to 6.0%.

23. The phase-change particulate slurry of claim 22 wherein the saline solution is sodium chloride.

24. The phase-change particulate slurry of claim 22 wherein the percentage of ice particles in the slurry is between about 5% and 59.5%.

25. The phase-change particulate slurry of claim 22 further comprising a perfluorocarbon solution.

26. An apparatus for removing heat from a patient comprising:
   (a) a liquid vessel containing a phase-change particulate slurry;
   (b) means connected to the liquid vessel for delivering the phase-change particulate slurry internally to the patient;
   (c) means for continuously administering the phase-change particulate slurry from the liquid vessel to the patient until a desired amount of heat has been removed from the patient.

27. The apparatus of claim 26 wherein the phase-change particulate slurry further comprises a saline solution and ice particles, the saline concentration being in a range between about 0.5% to 6.0%.

28. The apparatus of claim 27 wherein the saline solution is sodium chloride.

29. The apparatus of claim 28 wherein the percentage of ice particles in the phase-change particulate slurry is between about 5% and 59.5%.

30. The apparatus of claim 26 wherein the phase-change particulate slurry further comprises a perfluorocarbon solution.

31. The apparatus of claim 26 further comprising means for cooling the liquid vessel.

32. The apparatus of claim 26 further comprising means for mixing contents within the liquid vessel.

33. The apparatus of claim 27 wherein the saline concentration is about 0.9%.

34. The apparatus of claim 28 wherein the saline concentration is about 0.9%.

35. The apparatus of claim 28 wherein the percentage of ice particles in the phase-change particulate slurry is between about 5% and 59.5%.

36. The apparatus of claim 34 wherein the percentage of ice particles in the phase-change particulate slurry is between about 5% and 59.5%.

37. An apparatus for removing heat from a patient comprising:
   (a) a liquid vessel containing a phase-change particulate slurry;
   (b) means connected to the liquid vessel for delivering the phase-change particulate slurry internally to the patient, whereby the phase-change particulate slurry is delivered from the liquid vessel to the patient until a desired amount of heat has been removed from the patient.

38. The apparatus of claim 37 further comprising means for cooling the liquid vessel.

39. The apparatus of claim 37 further comprising means for mixing contents within the liquid vessel.

40. The apparatus of claim 37 wherein the phase-change particulate slurry comprises a saline concentration of about 0.9%.

41. The apparatus of claim 37 wherein the percentage of ice particles in the phase-change particulate slurry is between about 5% and 59.5%.

42. The apparatus of claim 40 wherein the percentage of ice particles in the phase-change particulate slurry is between about 5% and 59.5%.

43. An apparatus for administering a phase-change particulate slurry to a patient comprising:
   (a) a liquid vessel containing a phase-change particulate slurry;
   (b) a delivery device including a flexible, tubular member connected to the liquid vessel for delivering the phase-change particulate slurry internally to the patient, the flexible, tubular member having a first end and a second end, the first end insertable inside a patient, and the second end connected to the liquid vessel and in fluid communication with the liquid vessel, whereby the phase-change particulate slurry is delivered from the liquid vessel through the flexible, tubular member and into the patient until a desired amount of heat has been removed from the patient.

44. The apparatus of claim 43 wherein the flexible tubular member is adapted to be inserted into the gastrointestinal tract of the patient.

45. The apparatus of claim 43 wherein the flexible tubular member is adapted to be inserted into the trachea of the patient.

46. The apparatus of claim 43 wherein the flexible tubular member is adapted to be inserted into the patient intravascularly.

47. The apparatus of claim 42 wherein the flexible tubular member is adapted to be inserted into the patient subcutaneously.

48. The apparatus of claim 43 wherein the phase-change particulate slurry comprises a saline concentration of about 0.9%.

49. The apparatus of claim 43 wherein the percentage of ice particles in the phase-change particulate slurry is between about 5% and 59.5%.

50. The apparatus of claim 49 wherein the percentage of ice particles in the phase-change particulate slurry is between about 5% and 59.5%.

* * * * *